(12) United States Patent
Hwang et al.

(10) Patent No.: US 9,750,586 B2
(45) Date of Patent: Sep. 5, 2017

(54) ATTACHABLE TOOTHBRUSH'S POSTURE OR MOVEMENT TRACKING DEVICE

(71) Applicant: XiuSolution Co., Ltd, Yongin-si (KR)

(72) Inventors: Jin-Sang Hwang, Suwon-si (KR); Tae-Ho Yoon, Yongin-si (KR)

(73) Assignee: XiuSolution Co., Ltd., Yongin-si (KR)

( * ) Notice: Subject to any disclaimer, the term of this patent is extended or adjusted under 35 U.S.C. 154(b) by 119 days.

(21) Appl. No.: 14/396,049

(22) PCT Filed: Jul. 7, 2014

(86) PCT No.: PCT/KR2014/006038
§ 371 (c)(1),
(2) Date: Oct. 21, 2014

(87) PCT Pub. No.: WO2015/005620
PCT Pub. Date: Jan. 15, 2015

(65) Prior Publication Data
US 2015/0351883 A1 Dec. 10, 2015

(30) Foreign Application Priority Data

Jul. 9, 2013 (KR) .................. 10-2013-0080114
Jul. 9, 2013 (KR) .................. 10-2013-0080126

(51) Int. Cl.
*A46B 15/00* (2006.01)
*A61C 17/22* (2006.01)
(Continued)

(52) U.S. Cl.
CPC ............ *A61C 17/221* (2013.01); *A46B 13/02* (2013.01); *A46B 15/0002* (2013.01);
(Continued)

(58) Field of Classification Search
CPC ............ A46B 15/0002; A46B 15/0004; A46B 15/0006; A46B 15/0038; A46B 15/0055;
(Continued)

(56) References Cited

U.S. PATENT DOCUMENTS 5,331,707 A 7/1994 Irizarry
5,355,544 A 10/1994 Dirksing
(Continued)

FOREIGN PATENT DOCUMENTS

JP 2005-152217 6/2005
KR 10-2007-0054226 5/2007
(Continued)

*Primary Examiner* — Laura C Guidotti
(74) *Attorney, Agent, or Firm* — Goldilocks Zone IP Law

(57) ABSTRACT

An attachable apparatus for tracking posture or movement includes a housing having an accommodation space; a sensor in the accommodating space to sense a moving object's posture or movement; a sensing circuitry in the accommodating space to process sensing signals; and a fastening member for detaching the housing from the moving object. Wherein the fastening member includes an object insertion groove that guides the sensor to be matched with the moving object according to a predetermined direction, a fastening member comprised of elastic material allowing detachment from variety of different size moving objects, and a housing coupling member to combine moveable object with the housing.

15 Claims, 8 Drawing Sheets

(51) Int. Cl.
*G01P 15/18* (2013.01)
*A46B 13/02* (2006.01)
*G01N 29/44* (2006.01)
*G01N 29/48* (2006.01)

(52) U.S. Cl.
CPC ........ *A46B 15/004* (2013.01); *A46B 15/0006* (2013.01); *G01N 29/4436* (2013.01); *G01N 29/48* (2013.01); *G01P 15/18* (2013.01); *A46B 2200/1066* (2013.01); *G01N 2291/02827* (2013.01)

(58) Field of Classification Search
CPC ............ A46B 17/02; A46B 2200/1066; A61C 17/221; A61B 2562/0252; A61B 5/682; G01P 15/18; G09B 19/0084
USPC .............................................. 15/246; 702/153
See application file for complete search history.

(56) References Cited

U.S. PATENT DOCUMENTS

| | | |
|---|---|---|
| 5,784,742 A | 7/1998 | Giuliani et al. |
| 5,864,288 A | 1/1999 | Hogan |
| 6,199,239 B1 | 3/2001 | Dickerson |
| 6,327,734 B1 | 12/2001 | Mejinniss, III et al. |
| 6,536,068 B1 | 3/2003 | Yang et al. |
| 6,786,732 B2 | 9/2004 | Savill et al. |
| 7,976,388 B2 * | 7/2011 | Park .................... A46B 15/0002 15/105 |
| 8,175,840 B2 | 5/2012 | Hwang et al. |
| 2009/0241278 A1 | 10/2009 | Lemchen |
| 2011/0010875 A1* | 1/2011 | Iwahori .............. A46B 15/0006 15/22.1 |
| 2012/0171657 A1 | 7/2012 | Ortins et al. |
| 2013/0025078 A1 | 1/2013 | Heil et al. |

FOREIGN PATENT DOCUMENTS

| | | |
|---|---|---|
| KR | 10-2009-0051342 | 5/2009 |
| KR | 10-2009-0085403 | 8/2009 |
| KR | 10-2013-0014690 B1 | 2/2013 |
| WO | WO2006/137648 A1 | 12/2006 |
| WO | WO2009/066891 | 5/2009 |
| WO | 2011/149776 B1 | 12/2011 |

* cited by examiner

[FIG. 1]
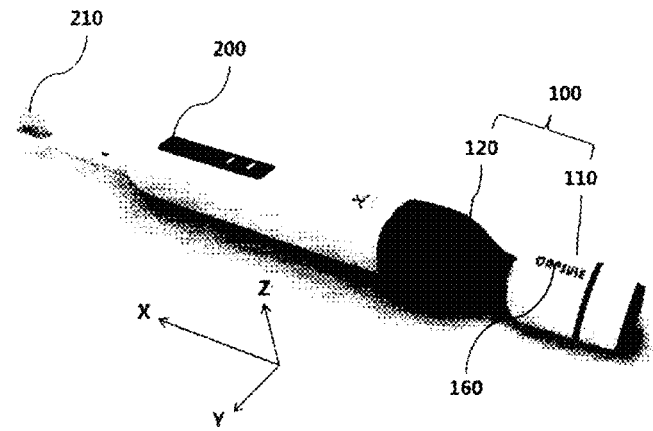
[FIG. 2]
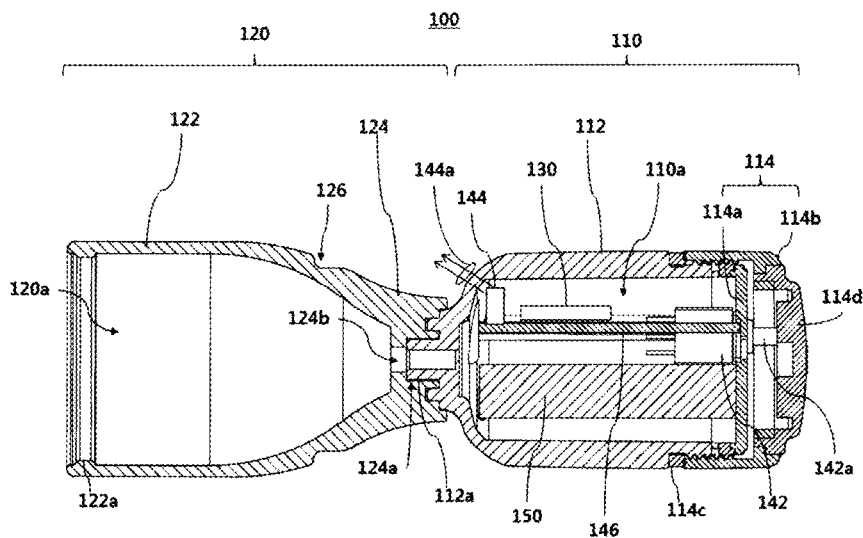
[FIG. 3]
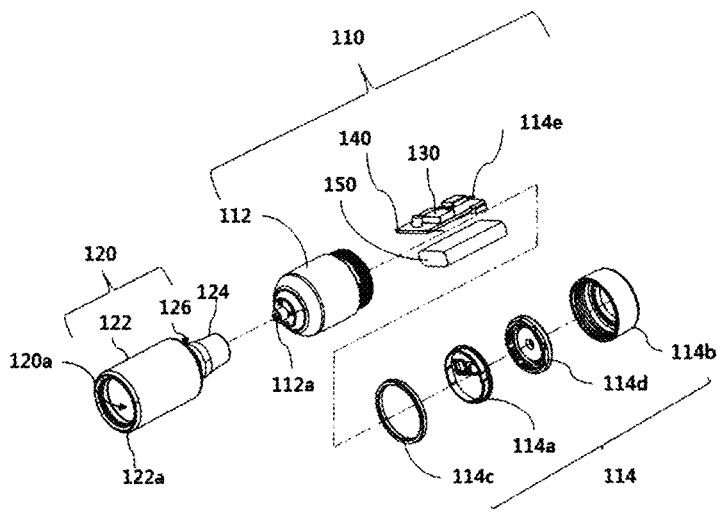

[FIG. 4]
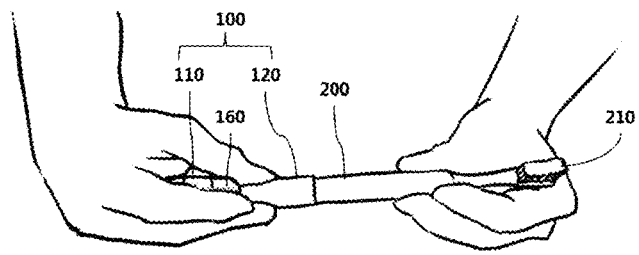
[FIG. 5]
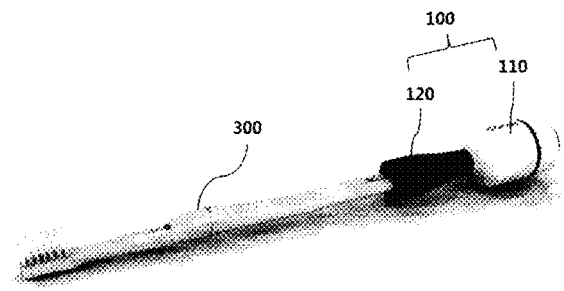
[FIG. 6]
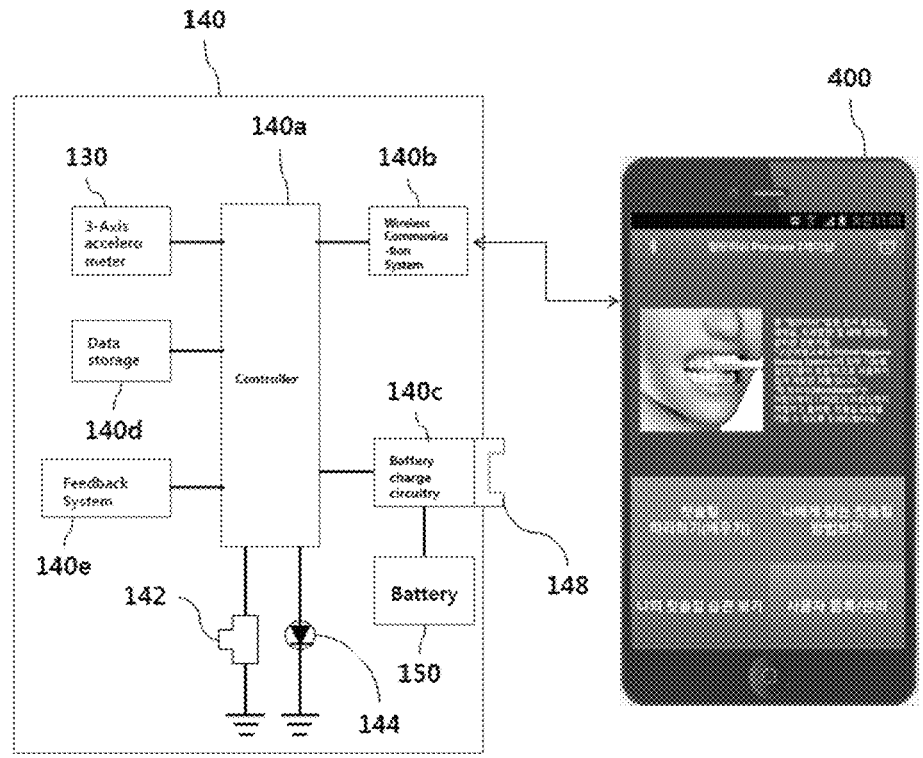

[FIG. 7]
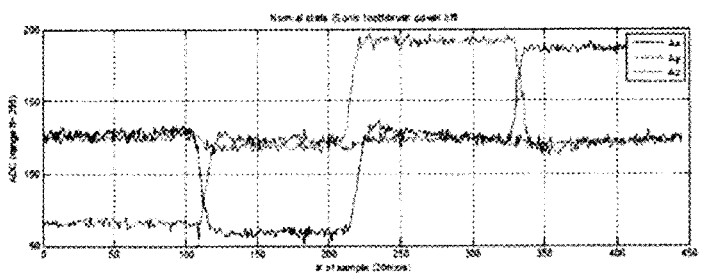
[FIG. 8]
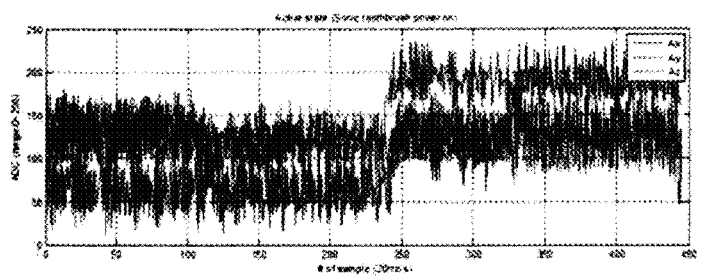
[FIG. 9]
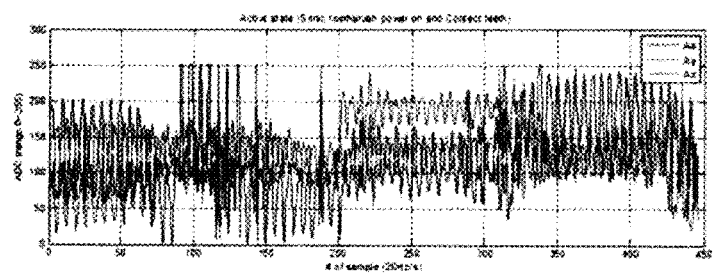

[FIG. 10]
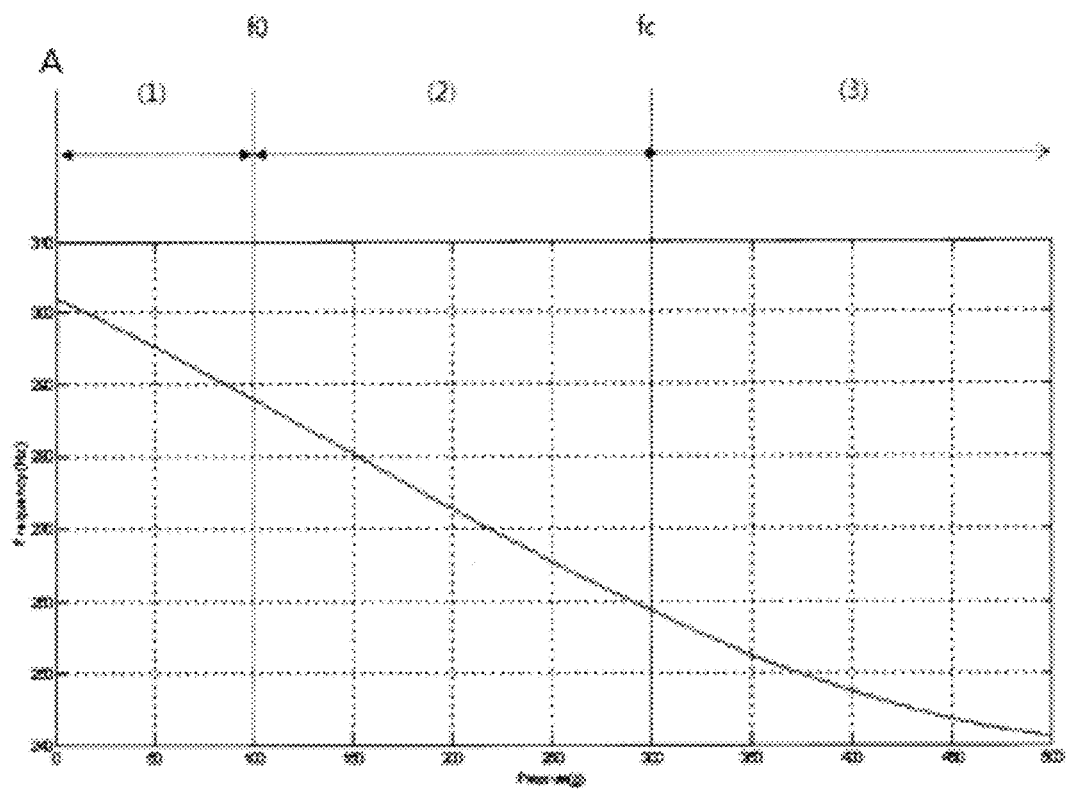

[FIG. 11]
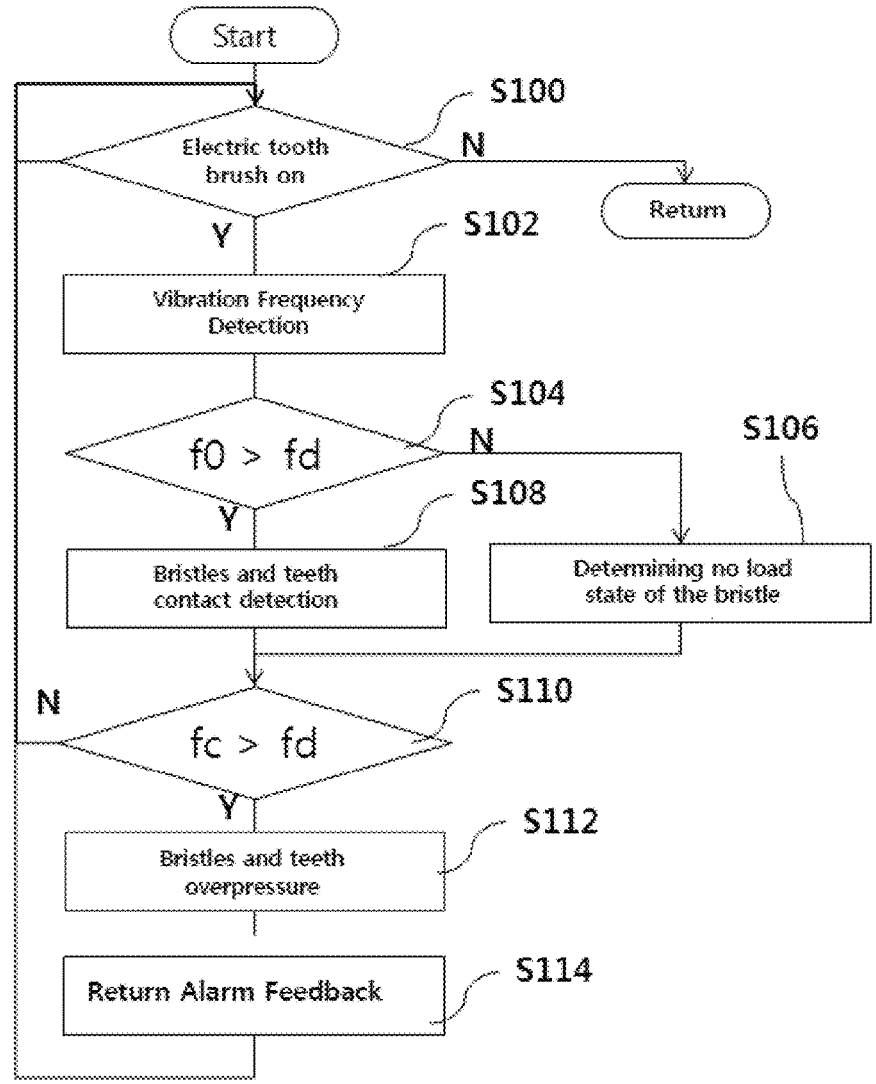
[FIG. 12]
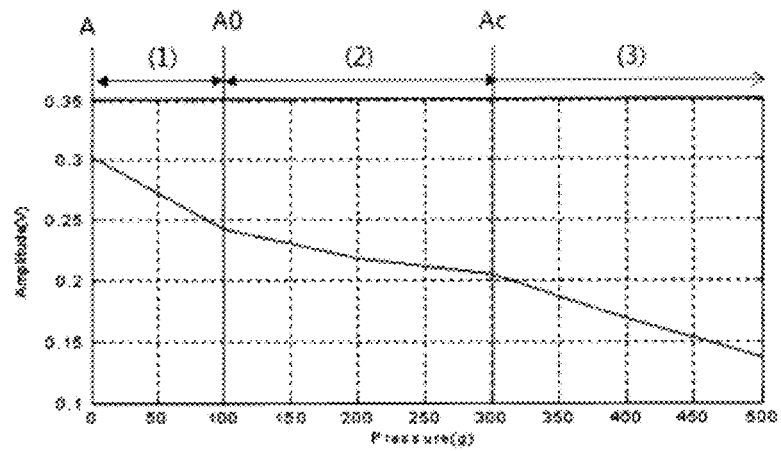

[FIG. 13]
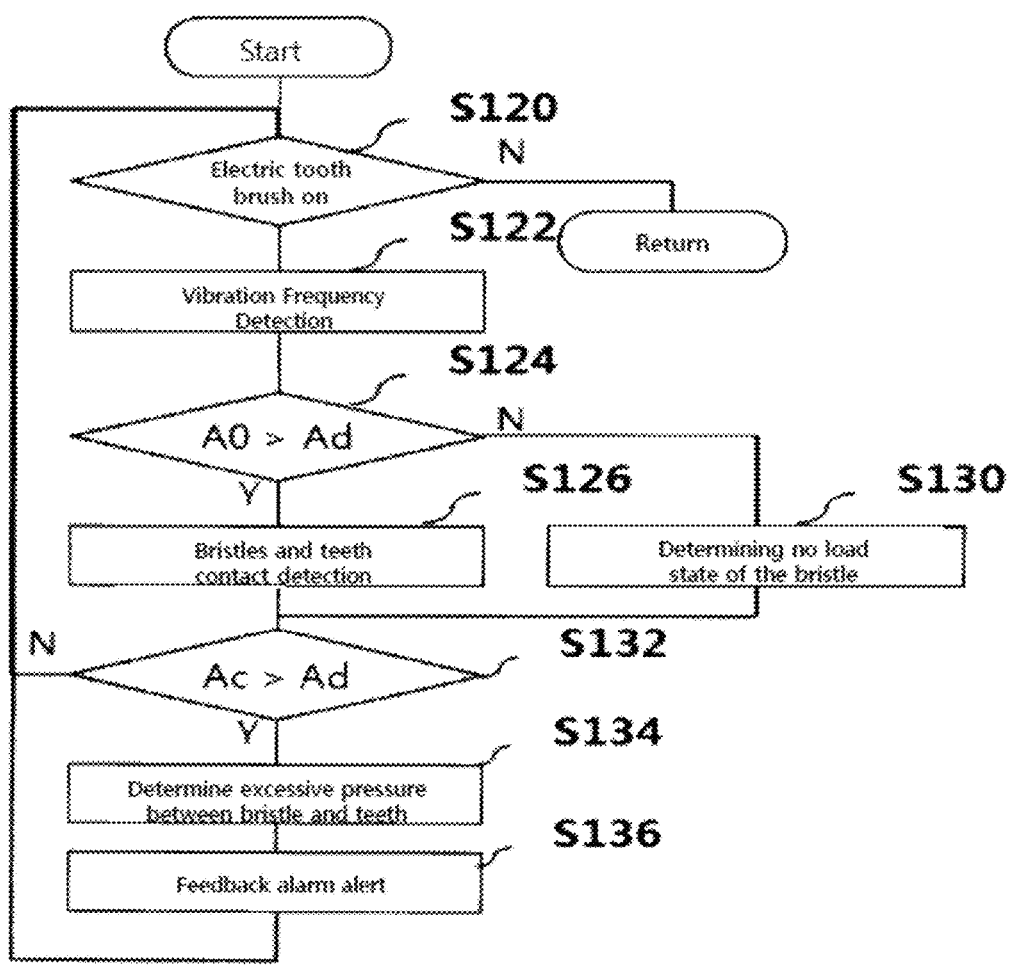

FIG. 14]
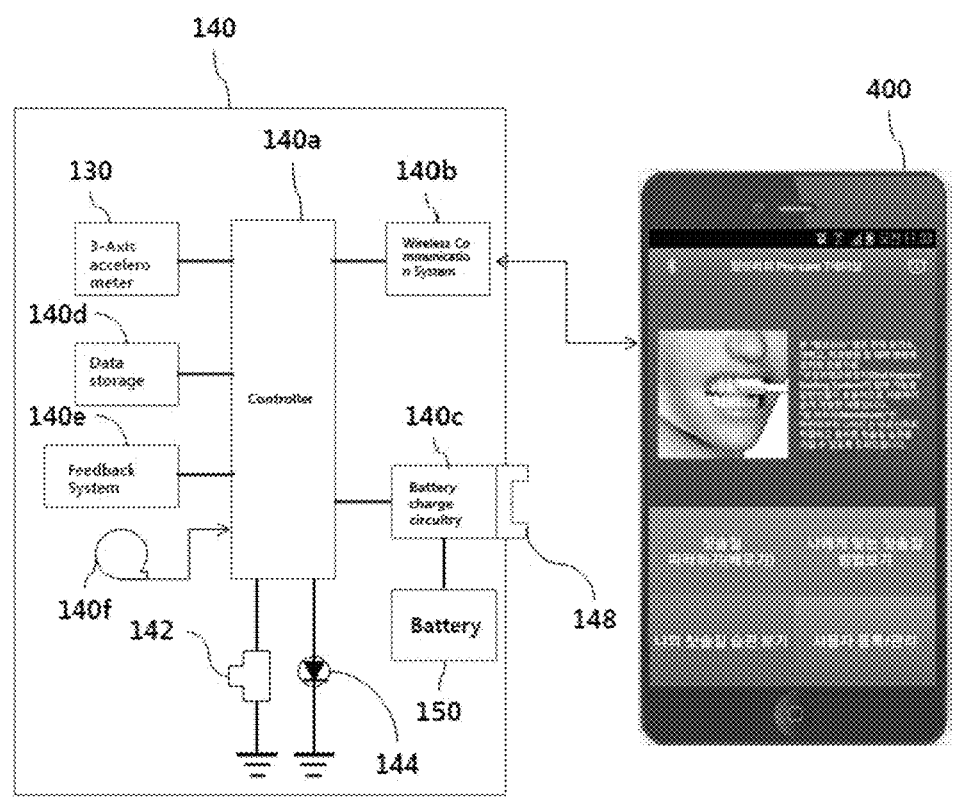

[FIG. 15]
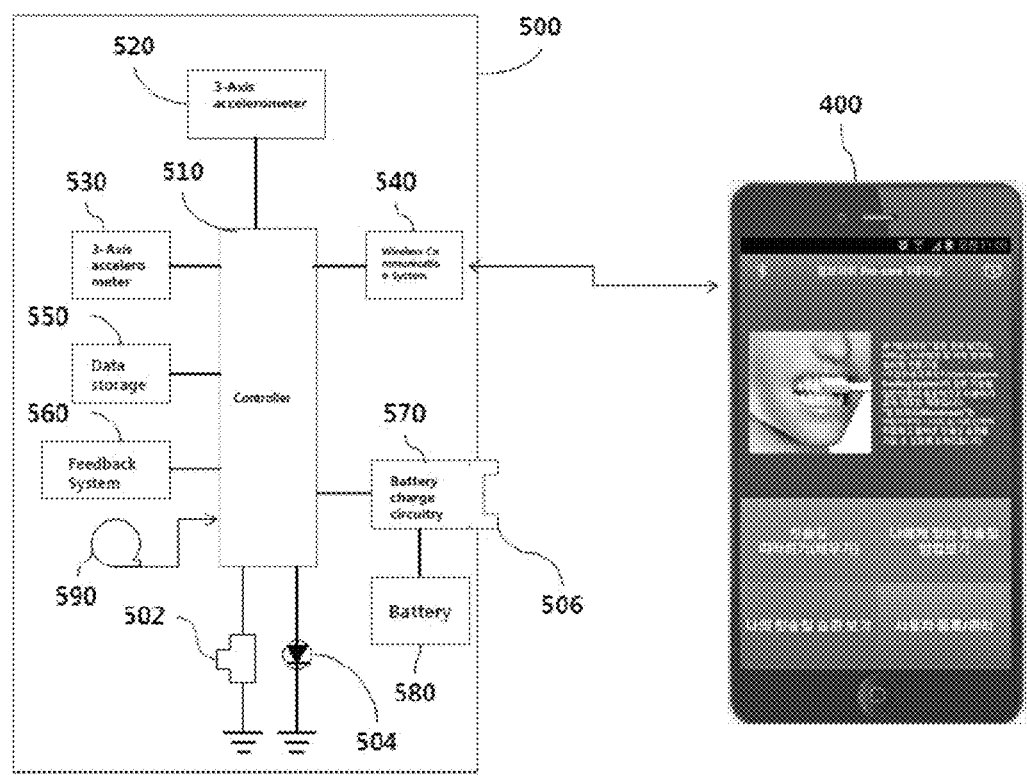

ATTACHABLE TOOTHBRUSH'S POSTURE OR MOVEMENT TRACKING DEVICE

CROSS REFERENCE TO RELATED PATENT APPLICATIONS

This application claims the benefit under 35 U.S.C. Section 371, of PCT International Application No. PCT/KR2014/006038, filed Jul. 7, 2014, which claimed priority to Korean Patent Application No. 10-2013-0080126, filed Jul. 9, 2013, and Korean Patent Application No. 10-2013-0080114, filed Jul. 9, 2013, the disclosures of which are hereby incorporated by the references.

TECHNICAL FIELD

The present invention relates to an attachable posture or movement tracking device and an electric toothbrush. More specifically, embodiments are related to attachable posture or movement tracking device and an electric toothbrush include a three-axis accelerometer, and detachable attached to the electric toothbrush like device to track position or movement of a moving device.

BACKGROUND

For reasons of dental health, orthodontic toothbrush technology, that can detect incorrect way of brushing teeth by detecting wrong posture or movement, has been recently been introduced. Such orthodontic toothbrushes include complex and expensive sensors to determine exact position of the toothbrush. These sensors require power to collect data and usually are attached to an electronic toothbrush.

Because the electric motor and the sensors are combined internally, there is a high production cost of the orthodontic toothbrush and hindering its widespread.

In addition, there are limitations in making orthodontic toothbrush due to different preferences of customers and different makers of toothbrush. Additionally, in cases of ultrasonic toothbrush or high vibration electronic toothbrush, sensors have difficulty sensing posture or movement due to its high vibration.

Thus, systems or methods for diagnosing toothbrushing habits and pattern have been proposed. However, prerequisite technology that can easily be used with variety of toothbrushes, which can meet a variety of user preferences, to detect or track toothbrushing posture or movement is required.

DESCRIPTION

In order to solve the above problems, the purpose of the presented invention is to provide an attachable apparatus that can be used with variety of different makers of non-electronic or electronic toothbrushes alike for detecting posture or movement of the apparatus.

Another purpose of the invention is to a posture or moving object tracking apparatus may feedback load state information by detecting a load state of the moving object.

Another purpose of present invention is to provide a toothbrush that can detect contact state or pressure of the bristle on teeth and provide feedback.

According to an aspect of the present invention, an attachable apparatus attached to a movement object for tracking posture or movement of the moving object may include a housing having an accommodation space, a sensor in the accommodating space to sense a moving object's posture or movement, a circuitry in the accommodating space to process the sensed signal, and a detachable fastening member attached to the housing.

According to an aspect of the present invention, a fastening member includes a moving object insertion groove for guiding a sensor to be matched with the moving object according to a predetermined direction, an elastic fastening portion attachable/detachable from moving objects of different size, a housing fastening portion for fastening moving object with the housing.

According to an aspect of the present invention, the housing is a hollow cylindrical body coupled with an opening in a rear end, a housing connecting portion to be fastened to a fastening member in a front end, an inner cover for forming the accommodating space by covering a rear end of the housing,
a power knob switch protruding to the rear end from an inner cover, and a flexible waterproof cap covering the rear end of the housing allowing the power knob switch from outside.

According to an aspect of the present invention, the housing further includes a marker for guiding fastening direction when fastening the apparatus with the moving object. Herein, the marker is at least a printed symbol, letter, label or graphic on the outer peripheral surface of the housing or a displaying lamp projecting the marker outward from the accommodating space. Also the marker may be formed on the fastening member.

According to an aspect of the present invention, an apparatus may include the sensor, which is a three-axis sensor, a sensor circuitry including a circuit for converting sensor signal to moving object's posture or movement information, an wireless transmitter for transmitting the information in real time, a rechargeable battery, and rechargeable power supply for supplying power to the three-axis sensor and the wireless transmitter.

According to an aspect of the present invention, the circuit may detect a load state of the moving object in response to oscillation frequency or amplitude change of the sensed signal.

In addition, according to an aspect of the present invention, the circuit in the housing including a microphone accommodated in the housing for picking up a vibration noise generated from the moving object, and a controller for detecting a load state of the moving object in response to a frequency or an amplitude of the vibration noise from the microphone's pick-up signal.

According to an aspect of the present invention, an apparatus may further includes a wireless electric device to communicate with the communication circuitry, wherein the wireless communication circuit stores the detected information received in real time and generates a feedback signal according to the moving object position or movement. In addition, the wireless electrical device may be a wireless phone, an wireless tablet, an wireless laptop, or a personal computer. The wireless device may detect a vibration noise generated from the moving object attached to the house through a microphone, and the controller generates a feedback signal according to the load state in response to the frequency of the noise signal picked up by the microphone.

According to another embodiment of the present invention, an apparatus coupled to the moving object for tracking a posture or movement of the moving object includes a housing having an accommodation space, a sensor in the accommodating space to sense a moving object's posture or movement, and a sensing circuitry in the accommodating space to process sensing signals, wherein the sensing circuitry detects a load state of the moving object in response to a vibration frequency or an amplitude of the sensed signals.

According to an aspect of the present invention, an apparatus coupled to the moving object for tracking a posture or movement of the moving object, the apparatus includes a housing, a sensor in the housing sensing a posture or a movement of the moving object in a predetermined direction, a microphone to detect a vibration noise generated by the moving object, and a posture or movement tracker to process the sensed signal from the sensor. A posture or movement tracking circuitry may determine a no-load or load state based on a vibration frequency or amplitude change through the microphone.

According to aspect of the present invention, an electric toothbrush may include a handle housing, a brush attached to a front end of the handle housing, a brush driver, for a vibrating, rotating or oscillating, in the handle housing, a brush posture or movement sensor in the handle housing, and a circuitry for determining a no-load or load state based on a vibration frequency or amplitude change and evaluates toothbrushing habit. In addition, the apparatus, according to an aspect of the present invention, the attachable posture or movement tracker may include a housing, a sensor in the accommodating space in a predetermined direction to sense a posture or movement of the brush, an elastic fastening member fastened on the outside of the housing member having a fastening groove fastened to a rear end of the housing handle and having a matching center axis with the sensing sensor, and a toothbrushing habit evaluator circuitry in the housing to evaluate the brush's posture or movement through the sensed signals. Herein, the toothbrushing habit evaluator circuitry may determine a no-load or load state according to change in the oscillation frequency or amplitude included in the sensing signal.

According to an aspect of the present invention, an electric toothbrush may include a handle housing a brush attached to a front of the handle housing, a brush driver for vibrating, rotating or oscillating the brush in the handle housing, a brush posture or movement sensor in the handle housing, and a circuitry for determining a no-load or load state based on a vibration frequency or amplitude change and for evaluating toothbrushing habit.

According to an aspect of the present invention, an electric toothbrush may include an handle housing, a brush coupled to a front end of the handle housing, a driver provided in the handle housing for rotating, vibrating, or oscillating the brush, a microphone in the handle housing and configured to detect the vibration noise, and a circuitry for determining no-load or load state of the brush according to change in vibration frequency or noise amplitude detected by the microphone.

Effects of the Invention

According to embodiment of the present invention, an attachable moving object posture or movement tracking apparatus, using elastic fastening member, may detect or track a posture or movement of the moving object, regardless of size, shape, makers, or model of the movement.

In addition, sensing error can be prevented due to high vibration is being reduced by elastic member. Additionally, in cases of ultrasonic toothbrush or high vibration electronic toothbrush, sensors have difficulty sensing posture or movement. The controller determines an over contact pressure state if the detected oscillation frequency is below than threshold oscillation frequency. If the determination is over contact state, the controller feedbacks a warning alarm through the feedback, thereby tooth health can be improved.

BRIEF DESCRIPTION OF THE FIGURE

FIG. 1 is a picture of an attachable moving object posture or movement tracking apparatus according to an aspect of the present invention.

FIG. 2 is a cross-sectional view of the attachable moving object posture or movement tracking apparatus of FIG. 1

FIG. 3 is an exploded perspective view of the removable Vehicle posture or motion of the first tracking device 100.

FIG. 4 is a view for explaining a matching process of Z-axis the toothbrush when fastening the fastening member 200 to the attachable moving object posture or movement tracking apparatus 100.

FIG. 5 illustrates a fastening member 120 is replaced with a manual toothbrush fastening member according to the present invention.

FIG. 6 illustrates a block diagram a circuitry part 140 is mounted on the circuit board of FIG. 3.

FIG. 7 shows a waveform diagram of a three-axis sensing signal with the power-off state of the electric toothbrush.

FIG. 8 shows a waveform diagram of a three-axis sensing signal with a power-on and no-load state of the electric toothbrush.

FIG. 9 shows a waveform diagram of a three-axis sensing signal with a power-on and load state of the electric toothbrush.

FIG. 10 is a variation curve of a vibration frequency based on contact pressure variation between a bristle and tooth according to an aspect of the present invention.

FIG. 11 is a flow diagram of an over contact pressure detection program between a bristle and tooth based on an oscillation frequency variation according to an aspect of the present invention.

FIG. 12 is a graph showing changes in the amplitude curve in accordance with changes in contact pressure of the brush head and a tooth FIG. 13 is a flow chart for illustrating an excessive pressure detection program between the bristle and tooth based on the amplitude variations according to an aspect of the present invention.

FIG. 14 shows a block diagram of a moving object posture or movement tracking apparatus according to an aspect of the present invention.

FIG. 15 illustrates a block diagram of an electronic brush tooth according to an aspect of the present invention.

DETAILED DESCRIPTION

In embodiments of the invention disclosed in the body for, specific structural and functional description are to be exemplified for describing the embodiments of the invention only the purpose, embodiments of the present invention may be embodied in various forms and the body of are not to be construed as limited to the described embodiment. Illustrated in the drawings can have a variety of changes may be added a variety of forms, specific embodiments and examples will be described in detail in the body of the present invention. This, however, is by no means to restrict the particular starting form of the invention, shall be understood to include all the changes that are included in the spirit of the invention and scope of equivalents to substitute.

Embodiments of the present invention now will be described more fully with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout this application.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure, and are not to be construed as limiting. Unless otherwise noted, the terms "a" or "an," as used in the specification and claims, are to be construed as meaning "at least one of." It is to be understood that the terms "including" and "having" do not preclude the addition of one or more components, features, steps, or integers or groups thereof and that the terms are to be construed as specifying components, features, steps or integers.

Unless otherwise defined, all terms, including technical and scientific terms, used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be described in detail with reference to the accompanying drawings.

FIG. 1 illustrates a picture of an attachable tracking apparatus 100 for posture or movement of the moving object, according to an embodiment of the invention, FIG. 2 illustrates a cross-100. sectional view of the tracking apparatus 100, FIG. 3 illustrates an exploded perspective view of the tracking apparatus Referring to the figures, the attachable moving object posture or movement tracking apparatus 100 can be attached to the rear end of a moving object 200, such as a toothbrush or an electric toothbrush. The attachable moving object posture or movement tracking apparatus 100 may include a housing 110 and a fastening member 120.

The housing 110 may include a rear open hollow cylindrical body 112 and a cover 114. The center of the front end of the hollow cylindrical body 112 is formed an engaging projection 112a. The fastening member 120 is fastened to the engaging projection 112a and is fixed with a screw. A plurality of anti-rotation projections may be formed around the engaging projection 112a.

The cover 114 may be a double cover, which are an inner cover 114a and an outer cover 114b. The inner cover 114a is assembled to engage with the inner peripheral surface of the hollow cylindrical body 112. The outer cover 114b via the O-ring 114c to the rear end of the outer peripheral surface of the hollow cylindrical body 112 are screwed to form a waterproof inner space 110a of the housing 110. A flexible member 114d is integrally formed at the center of the outer cover 114b by a double injection molding. A flexible member 114d presses a switch knob 142a elastically by an external pressure, and is returned to its original position when the external force is released.

A circuitry part 140 may include a 3-axis sensor circuit 130, a power switch 142, an operation display lamp 144, and circuit components. A printed circuit board 146 including the circuitry part 140 and the battery 150, etc. may be housed in the inner space 110a. A power switch knob 142a, a mini-USB socket (not shown) and a mini memory card connector (not shown) may be installed on the inner cover 114a.

The fastening member 120 is made of elastic silicone rubber material with an open front end and a hollow cylindrical rear end.

The fastening member 120 includes a moving object fastening portion 122, a housing fastening portion 124, a vibration damping portion 126 in between, and a fastening groove 120a extended rearward from the front end of the fastening member 120. The moving object fastening portion 122 may have the cylindrical shape with an inner diameter smaller than the minimum diameter of the handle of an electric toothbrush in the current market. A protruding circular rim 122a is formed at the end of the moving object fastening portion 122. The housing fastening portion 124 is cone shaped and has an engaging groove 124a in the rear. The housing fastening portion 124 includes an engaging groove 124a and a through screw hole 124b extended from the fastening groove 120a.

Accordingly, the fastening member 120 is secured to the front end of the engaging projection 112a of a moving object 112 that is inserted into an engaging groove 124a through a screw hole 124b. The vibration damping portion 126 attenuates the vibration energy generated from the electric toothbrush 200 in the form of the annular groove so as to have a thinner thickness than the thickness of the moving object fastening part 122. Thus, preventing malfunction due to the vibration energy in the sensor 130 in the housing 110. In particular, in the electric toothbrush in the high vibration with an ultrasonic drive unit largely affects the sensing operation of the three-axis sensor, according to an aspect of the present invention, the vibration damping structure can sense a posture and movement of the moving object more accurately.

Once a moving object 200 is inserted into the fastening groove 120a, the fastening member 120 maintains a fastening state by extending the moving object fastening portion 122 and exerting pressure with protruding circular rim 122a to the moving object 200. Therefore, the fastening member 122 is a silicon rubber elastic material and can be fastened to the electric toothbrush, the moving object 200, of different shape and size toothbrush from different manufacturers.

An outer circumferential surface of the housing 110 includes a display unit 160 for guiding a fastening direction of the moving object for fastening to the moving object. The display unit 160 may be a printed symbol, character, label or graphic on the outer circumferential surface. In an embodiment of the present invention, printed characters are printed on the outer circumferential surface of the housing 110. Also, a light, from operation indicator lamp 144 installed in the inner space 110a, is projected in a direction that matches the character printed on the housing 110.

Therefore, a printed circuit board 146 is assembled in the housing 110 so the X axis of the three-axis sensor 130 matches the arrangement direction of character of the display unit 160, that is, the X-axis direction and the display unit 160 is to be arranged above the Z-axis of the 3-axis sensor 130. Therefore, the housing 110 from the outside of the display unit 160, the character printing position or by the light emission display of the operation display lamp 144, a 3-axis position of the 3-axis sensor 130 can be seen. A central axis of the fastening groove 120a of the fastening member 120 is automatically aligned to the X-axis of 3-axis sensor 130 when fastening to the housing 110.

FIG. 4 is a view for describing a Z-axis matching process when fastening the moving object 200 to the attachable moving object or movement tracking apparatus 100 according to an aspect of the present invention.

Referring to FIG. 4, when fastening the fastening member 120 to a moving object 200, the moving object 200 inserts and aligns in an x-axis direction of the fastening groove 120a and the moving object 200, the bristle 210 fastens to align with marker 160 in a z-axis. Likewise, the posture of the movement of the fastened housing 110 and the moving object 200 can be sensed by the sensor 130 accommodated inside the housing 110.

FIG. 5 illustrates a fastening member 120 is replaced with a manual toothbrush fastening member according to the present invention.

As shown in FIG. 5, a manual toothbrush fastening member has a smaller diameter than the diameter of the fastening member of the above-mentioned electric toothbrush.

FIG. 6 shows a block diagram that the circuitry part 140 is mounted on the printed circuit board of FIG. 3 according to an aspect of the present invention.

Referring to FIG. 6, the circuitry part 140 may include a controller 140a, a wireless communicator 140b, charger 140c, a storage 140d, and a feedback unit 140e according to an aspect of the present invention The controller 140a, which includes a complete microcomputer or microprocessor, controls the circuitry part 140.

A communicator 140b includes a Bluetooth communication method for communicating with a smart phone 400. According to another embodiment, NFC communication method, ZigBee and short-range wireless communication method, a wireless Wi-Fi method or the wireless LAN method can be used as communication method.

The charger 140c receives an external power from through the micro USB connector 148 and charges a battery 150, and supplies a stable operating voltage to preventing from overcharge and over-discharge.

The controller 140a can download or upload data to/from an external computer connected to a wired connector with the micro USB 148.

The storage 140d may include a micro SD card and a card connector, and store the sensed data.

The Feedback unit 140e is for generating a feedback signal by the visual, auditory or haptic, for example, may include a buzzer for generating an alarm sound, alarm display lamp, a speaker, or a vibration motor.

By performing a moving object posture or movement detection program, sensing signal sensed by the 3-axis sensor 130 can digitally converted in real time and be sent to smart phone 400 through wireless communication unit 140b or stored in the storage unit 140d. The controller 140a controls the display lamp 144 in response to a power switch 142, and supplies a power to a 3-axis sensor 130, a wireless communicator 140b, the control supply 140d, and a feedback section 140e, from the battery 150.

Using a tracking application program installed on a Smartphone 400, the Smartphone 400 analyzes sensed signal received from the three-axis sensor using BLUETOOTH technology and displays the analyzed result on a display.

The Posture and movement tracking and control application program is disclosed in the application, Republic of Korea Patent Application No. 2007-0117688, Apparatus of chasing posture of moving material object, method of chasing posture of moving material object, apparatus of chasing posture of toothbrush and method of chasing posture of toothbrush using the same, and Republic of Korea Patent Application No. 2007-7007094, tooth brushing pattern analyzing/modifying device, method and system for interactively modifying tooth brushing behavior filed by the present inventors the posture and motion tracking and management program pattern analysis on calibration device, method and system calibration interactive brushing habits that have been disclosed, thus, detailed example is omitted.

In addition, the controller 140a may perform a program detecting the pressure exerted on the tooth brush by analyzing posture or movement of moving object based on data of the 3-axis sensor, vibration sensor 130, such as an acceleration sensor control section 140a operation and detecting changes in the vibration frequency or amplitude.

FIG. 7 shows a waveform diagram of a 3-axis sensing signal with the power-off state of the electric toothbrush. FIG. 8 shows a waveform diagram of a 3-axis sensing signal with the power-on no-load condition of the electric toothbrush, and FIG. 9 shows a waveform diagram of a three-axis sensing signal with a power-on load of the electric toothbrush. As shown in FIG. 7, during power off state, electric toothbrush only displays long signal waveform in accordance with change in posture. When the electric toothbrush is on, as shown in FIGS. 8 and 9, posture waveform is overlapped with frequency signal that has short period. It is shown that frequency signal of no contact state wherein the bristle and teeth do not touch (no-load state) of FIG. 8 is shorter than that of contact state wherein the bristle and teeth touch (load state) of FIG. 9.

FIG. 10 illustrates a variation curve of the electric toothbrush in accordance with the oscillation frequency change of the contact pressure of the toothbrush on tooth.

Referring to FIG. 10, it shows that, when no load, 302 Hz of the vibration frequency decreases to 259 Hz if the pressure of 300 g and reduces to 241 Hz when the pressure of 500 g, respectively.

Generally, when supplying a power to the electric toothbrush having a driving part, a predetermined range of oscillation frequency such as "A," is generated by the driving unit or oscillation unit and the oscillation frequency is changed according to a pressure applied on bristles of the toothbrush. Therefore, the predetermined range of oscillation frequency range may be defined as a no-load state, as shown in section 1 of FIG. 10. Because, it is recommended that power-on operation is followed by slightly touching the tooth brush on the tooth after applying toothpaste on the bristles of the electric toothbrush or locating the tooth brush in the mouth. There is a problem of scattering toothpaste by strong vibration of the toothbrush, if not powered inside of the mouth after applying the toothpaste. Therefore, the reason is for setting a predetermined frequency range f0 for a contact start period with the teeth. In addition, section 2 interval which indicates a period that the electric toothbrush contacts with the tooth, therefore the period is for measuring actual brushing time.

The value of f0, value effectively used to measure time spent correctly brushing teeth, and the value of fc, value used to differentiate between excessive pressure on the bristle and measure time spent incorrectly teeth brushing, can be experimentally predetermined depending on shape, intensity and intensity of the bristle. It can be seen that the frequency becomes lower in inverse proportion to the intensity of brushing teeth with high pressure, load on bristle.

FIG. 11 is a flow diagram of an excessive or over contact pressure detection program between a bristle and tooth according to an oscillation frequency variation of an aspect of the present invention.

Referring to FIG. 11, a controller 140a transmits a 3-axis sensing signal corresponding to the posture of the electric toothbrush 200 from the three-axis sensor 130 to the smartphone 400 through the wireless communicator 140b in real time. The controller 140a detects an oscillation frequency fd S102 when a power is supplied S100 to the vibration source of the electric toothbrush 200. The controller 140a determines as a no-load state if the detected vibration frequency is higher than no load oscillation frequency f0, a contact state if the detected vibration frequency is lower than the no load oscillation frequency f0, or an over contact pressure state if the detected vibration frequency falls below than the threshold vibration frequency fc S106. The controller 140 a determines an over contact pressure state if the detected oscillation frequency fd is below than threshold oscillation frequency fc S108. If the determination is over contact state, the controller 140a feedbacks a warning alarm through the feedback section 140e. The no load vibration frequency f0 and the threshold oscillation frequency fc may be set differently depending on the type of the electric toothbrush. Depending on the toothbrush model, f0, no load vibration frequency, and fc, threshold vibration frequency, can be predetermined before use.

The table 1 shows a vibration frequency characteristic according to makers.

TABLE 1

| Maker | Pressure | 0 g | 100 g | 200 g | 300 g | 400 g | 500 g |
|---|---|---|---|---|---|---|---|
| Company | Hz | 405 | 375(f0) | 365 | 315(fc) | 300 | 300 |
| Company B | Hz | 302 | 288(f0) | 273 | 259(fc) | 247 | 241 |

Therefore, according to an aspect of the present invention, detecting can be done as a touch state of the tooth brush to tooth if the oscillation frequency becomes lower than no-load frequency of oscillation of the electric toothbrush, and detects as an over contact pressure state if an oscillation of the electric toothbrush drops below a certain frequency the vibration frequency whether the pressure (e.g. at least 300 g). There is a benefit to giving user's attention by generating signal, such as auditory feedback, visual or tactile to the touch and when performed more than 300 g excessive brushing pressure is on the bristles.

In the above-described embodiment has been described as performing a brush head according to the vibration frequency changes in pressure contact with the teeth and the detection program in the control unit (140a), is not limited to, and also performed by the smart phone (400) and the feedback unit of the smart phone (400) can generate through a warning alarm.

FIG. 12 is a graph showing changes in the amplitude curve in accordance with changes in contact pressure of the brush head and a tooth.

Reference to FIG. 12, the figure shows that the amplitude decreases 0.3029V at no load to 0.2048V when the pressure of 300 g, and reduces to 0.1369V when the pressure at 500 g.

When supplied with power, driver or vibrator of the electronic tooth brush creates an amplitude 0.3029V or similar to 'A'. This amplitude 'A' decreases depending on the pressure applied to the bristle. Like section 1 of FIG. 12, predetermined amplitude range can be defined as a no-load state. It is recommended the toothbrush slightly touches the teeth or is placed inside the mouth before turning on the toothbrush. This is the reason for setting recommended amplitude range as start level A0 of 0.2433V. Additionally, section 2 represents amplitude of a contact area of teeth and bristle, and can effectively be used in measuring the toothbrushing time. Section 3 of FIG. 12, an area past point Ac, represents excessive pressure area where the bristle may wear out the teeth in contact.

An embodiment of the present invention, A0 and Ac, value used to differentiate between excessive pressure on the bristle and measure time spent incorrectly teeth brushing, can be experimentally predetermined depending on shape, intensity and intensity of the bristle.

It shows that the amplitude becomes smaller in inverse proportion to the intensity of brushing teeth with strong pressure.

FIG. 13 is a flow chart for illustrating a detection program for the bristle and excessive pressure on tooth according to the amplitude variations of an aspect of the present invention.

Referring to FIG. 13, the controller 140a transmits a sensed 3-axis signal to a smartphone 400 in real time through a wireless communicator, wherein the signal received from 3-axis sensor 130 and depends on posture of the electronic toothbrush 200. The controller 140a detects an amplitude Ad when power is supplied S120 to the electronic toothbrush 200 S122. If the detected amplitude is higher than the no-load amplitude A0 S124, the controller 140a determines a no-load state S130. If the detected amplitude is lower than the no-load amplitude A0, the controller 140a determines a tooth brushing state, a state in which the teeth and the bristle are in contact S126. If the detected amplitude Ad is lower than the threshold amplitude Ac S132, the controller 140a determines an excessive pressure on the teeth by the bristle S134. If an excessive pressure contact state is detected, the controller 140a sends a feedback signal S136 and warns through an alarm. The no-load amplitude A0 and a threshold amplitude Ac of the electronic toothbrush may be set differently depending on the brand. A model of electric toothbrush can be selected before use so as to select a no-load amplitude A0 or the threshold amplitude Ac corresponding to the electronic toothbrush being fastened to.

Table 2 shows the amplitude characteristic of the particular electric toothbrush

TABLE 2

| Maker | Pressure | 0 g | 100 g | 200 g | 300 g | 400 g | 500 g |
|---|---|---|---|---|---|---|---|
| Company A | Amplitude | 0.3029 | 0.2433(A0) | 0.2178 | 0.2048(Ac) | 0.1689 | 0.1369 |

According to an embodiment of the present invention, if the amplitude of electronic toothbrush drops below the no-load amplitude, it is detected as contact state between the bristle of the toothbrush and teeth and if vibration frequency drops below the predetermined vibration frequency, excessive pressure (e.g. more than 300 g) on the teeth from the bristle can be detected. Likewise, auditory, visual, tactile or other feedback may generate and warn the user when the bristle exerts more than 300 g of excessive pressure while brushing teeth.

In the above-described embodiment has been described as performing a detection program according to the vibration frequency changes in pressure contact with the teeth and the detection program in the controller 140a, which is not limited thereto, but, the smart phone 400 can perform the program and outputs a warning alarm by a feedback unit of the smart phone.

Likewise, when power is supplied to sonic, ultrasonic or other electric toothbrush, a driver of the toothbrush causes the bristle to vibrate and output its unique frequency or amplitude signal.

Like FIGS. 10 and 11, as pressure applied to bristle increases, frequency decreases in case of Medi screen 551 (Mediclean) class of OMRON's electric toothbrush and like FIGS. 12 and 13, as pressure applied to the bristle increases, the amplitude decreases in case of Philips Sonicare Elite e9800 professional's (elite e9800 professional). Therefore, the method of classification is different based on method or structure of vibrating of sonic toothbrush, supersonic toothbrush, and electronic toothbrush. For example, structure difference can be considered on of the reasons between Omron's Mediclean 551 that has a vibrator located in the end of the bristle and Philips' Sonicare elite e9800 professional that has vibrator in the handle housing.

FIG. 14 shows a block diagram of a moving object posture or movement tracking apparatus according to an aspect of the present invention.

Thus, FIG. 14 has the same configuration with FIG. 6 except the microphone 104f is further included. The remaining parts are similar to figures as mentioned above and will be labeled accordingly.

Except the controller 140a may perform a program for detecting intensity of pressure applied to the bristle by detecting frequency or amplitude change with the microphone 140f output data. In other words, like we used the sensor 130 output is used to measure vibration frequency or amplitude size in FIG. 6, the sensor 130 output is used to measure vibration frequency or amplitude size, the output of microphone 140f may be used to measure vibration noise frequency or amplitude size. This is possible, because the basic principle of measuring vibration with the acceleration sensor and a microphone are the same.

According to an aspect of the embodiment, a microphone 140f is additionally used, in order to increase the detecting efficiency or performance, in accordance with the situation, such as an electric toothbrush is applied, and detecting only one of the size or change in size of the amplitude of the frequency and the other is measuring the other by using a 3-axis sensor is a microphone.

The remaining part of the detailed description will be omitted since it is the same as FIG. 6

According to another embodiment, another embodiment of FIG. 14 is to determine teeth contact or teeth excessive pressure contact by analyzing the frequency or amplitude size of vibration noise frequency obtained from vibration noise through the microphones 140f when power-on. The process of determining is omitted since the process is the same as the explanations mentioned above.

Another example of noise detecting method is to use a microphone of the smartphone 400. The smart phone generates warning alarm, such as vibration or warning sound, or warning indicator, by performing excessive pressure contact state detecting program and using the feedback unit of the smart phone depending on the detected result.

FIG. 15 illustrates a block diagram of the electric toothbrush in accordance with an aspect of the present invention.

An electric toothbrush 500 includes a power switch 502, an operation display lamp 504, and a micro-USB connector 506. A circuitry part of the electric toothbrush 500 includes a controller 510, a bristle driver 520, a three-axis sensor 530, a wireless communicator 540, storage 550, a feedback unit 560, a charging circuit 570, a battery 580 and a microphone 590. The electric toothbrush 500 includes the above-described bristle driver 520 and the above described apparatus for tracking moving object or movement are integrally configured in a single body.

While driving a bristle of the toothbrush by controlling the bristle controller 520, the controller 510 may send the sensing signal, detected in the three-axis sensor 530, to the smart phone 400 via the wireless communicator 540. Similarly, the controller 510 detects an over pressure contact state either detecting changes in vibration frequency or amplitude by the 3-axis sensor 530 or detecting, or detecting changes in vibration or amplitude through a microphone 590, and may output an warning alarm through the feedback unit 560 using the detected result.

As described above, in order to give an understanding of the present invention, the technique is described for applying a moving object posture tracking apparatus to toothbrush posture tracking apparatus according to user's tooth brushing. However, this is merely illustrative, not only this tracking device moving object position tracking device can be applied is a toothbrush, but also applied, such as diet control and measurement devices for eating habits. Further an aspect of the present invention can be applied to different areas, for example, for tracking part or whole of the body, or for tracking posture or movement the object or the human body.

According to an embodiment of the present invention, attachable moving object's posture or movement detecting apparatus is applied to toothbrush posture tracking device or toothbrush posture tracking method and track the user's tooth brushing posture to track user's tooth brushing movement. In addition, electric toothbrush such as ultrasound toothbrush provide feedback by measuring the load on the bristle that is measuring users' intensity of tooth brushing to guide a correct electric toothbrush usage and accordingly, the detected user's tooth brushing movement can be applied to the tooth brushing movement analyzing device and can be used to analyze the user's tooth brushing movement. Likewise, electric toothbrush's actual tooth brushing time and correctly tooth brushing time can be used as the basis of premium service of insurance companies.

In addition, the attachable moving object posture or movement tracking apparatus can be applied to fork, knife, spoons and other objects to monitor eating habits. In addition, the attachable moving object posture or movement tracking device can also be applied to orthodontic devices and can be applied in areas in which require monitoring objects and part of a body's posture.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

EXPLANATION OF SYMBOL

100: attachable moving object posture or movement tracking apparatus
110: housing 120: moving object fastening member
130: 3-axis sensor 140: Circuitry part
150: Battery 160: display unit
200: moving object, electric toothbrush 210: tooth brush
300: Manual brush 400: Smart phone

What is claimed is:

1. An attachable apparatus, comprising:
a housing having an accommodation space; an inner cover to form the accommodating space by covering a portion of the housing;
a sensor disposed in the accommodating space and configured to sense at least one of posture or movement of a housing and generate a sensing signal;
a circuitry disposed in the accommodating space and configured to process the sensing signal;
a power switch coupled to the circuitry;
a flexible member covering the power switch to waterproof the power switch; and
an elastic fastening member including a first portion coupled with the housing and a second end portion coupled with a manual toothbrush handle,
wherein the second portion of the elastic fastening member having a toothbrush insertion groove configured to insert a portion of the manual toothbrush handle, and
wherein the housing has a hollow cylindrical body and a housing fastening portion of the a first portion of the elastic fastening member is configured to be coupled with the hollow cylindrical body.

2. The apparatus of claim 1, wherein the elastic fastening member is detachable from various types of the manual toothbrush handle via the toothbrush insertion groove.

3. The apparatus of claim 1, further comprising a marker for guiding the toothbrush to the predetermined direction when the toothbrush is coupled with the apparatus.

4. The apparatus of claim 3, wherein the marker is at least one of a printed symbol, a letter, a label and graphic on a surface of the housing or a displaying lamp projecting the marker outward from the accommodating space.

5. The apparatus of claim 1, wherein the sensor includes a three-axis sensor, and
wherein the circuitry includes a circuitry element processes the sensing signal, a wireless transmitter transmits the information and a power supply element configured to supply a electric power to at least one of the three-axis sensor and the wireless transmitter.

6. An attachable apparatus, comprising:
a housing having an accommodation space;
a sensor disposed in the accommodating space and configured to sense at least one of posture or movement of a toothbrush and generate a sensing signal;
a circuitry disposed in the accommodating space and configured to process the sensing signal; and
an elastic fastening member including one portion coupled with the housing and the other portion coupled with a toothbrush handle,
wherein the other portion of the elastic fastening member having a toothbrush insertion groove configured to insert a portion of the toothbrush handle,
wherein the sensor includes a three-axis sensor includes a circuitry element senses at least one of toothbrush's posture and movement information to the sensed signal, and
wherein the circuitry element detects a load state of the toothbrush in response to at least one of oscillation frequency and amplitude change of the sensed signal.

7. The apparatus of claim 6, wherein the circuitry element includes a microphone accommodated in the housing for picking up a vibration noise generated from the toothbrush, and a controller for detecting a load state of the toothbrush in response to at least one of a frequency and an amplitude of the vibration noise from the microphone.

8. The apparatus of claim 6, wherein the wireless transmitter configured to communicate with an external device and the external device stores the detected information received through the wireless transmitter and generates a feedback signal according to at least one of a position and a movement of the toothbrush.

9. The apparatus of claim 8, wherein the external device is at least one of a wireless phone, a wireless tablet, a wireless laptop, and a personal computer.

10. The apparatus of claim 8, wherein the external device configured to detect a vibration noise generated from the toothbrush attached to the housing through a microphone, and
wherein the circuitry element including a controller generates a feedback signal according to the load state in response to the frequency of the noise signal picked up by the microphone.

11. An attachable apparatus, comprising:
a housing having an accommodation space;
a sensor disposed in the accommodating space to sense at least one of a toothbrush's posture and movement; and
a sensing circuitry disposed in the accommodating space to process sensing signals of the sensor,
wherein the sensing circuitry detects a load state of the toothbrush in response to at least one of a vibration frequency and an amplitude of the sensed signals, and
wherein the sensor includes a three-axis acceleration sensor, and wherein the sensing circuitry includes a circuitry part converting a sensor signal to at least one of toothbrush's posture and movement information, a wireless transmitter transmits the information, and a battery supplies a power to the three-axis acceleration sensor and the wireless transmitter.

12. The attachable apparatus of claim 11, further comprising:
a microphone configured to detect a vibration noise generated by the toothbrush;
a posture or movement tracker configured to process the sensed signal from the sensor; and
a movement tracking circuitry configured to determine a no load or load state based on at least one of a vibration frequency and an amplitude change through the microphone.

13. The apparatus of claim 12 further comprising a marker for guiding the toothbrush to the predetermined direction when the toothbrush is coupled with the apparatus.

14. The apparatus of claim 11, further comprising:
an elastic fastening member including one portion coupled with the housing and the other portion coupled with a handle of the toothbrush; and
a marker for guiding the toothbrush to the predetermined direction when the toothbrush is coupled with the apparatus.

15. The apparatus of claim 14, wherein the elastic fastening member detachable from various types of the toothbrush handle, and further comprises a housing coupling member to combine moveable object with the housing.

* * * * *